United States Patent [19]

Allen

[11] Patent Number: 5,698,589
[45] Date of Patent: Dec. 16, 1997

[54] WATER-BASED TOPICAL CREAM CONTAINING NITROGLYCERIN AND METHOD OF PREPARATION AND USE THEREOF

[75] Inventor: Michael P. Allen, Pell City, Ala.

[73] Assignee: International Medical Innovations, Inc., Birmingham, Ala.

[21] Appl. No.: 594,304

[22] Filed: Jan. 30, 1996

Related U.S. Application Data

[63] Continuation-in-part of Ser. No. 69,409, Jun. 1, 1993, abandoned, and Ser. No. 398,872, Mar. 6, 1995, abandoned.

[51] Int. Cl.$^6$ .................................................. A61K 31/21
[52] U.S. Cl. .................................................. 514/509
[58] Field of Search .................................................. 514/509

[56] References Cited

U.S. PATENT DOCUMENTS

| | | | |
|---|---|---|---|
| 4,336,243 | 6/1982 | Sanvordeker et al. | 424/28 |
| 4,521,421 | 6/1985 | Foreman | 514/267 |
| 4,801,587 | 1/1989 | Voss et al. | 514/248 |
| 5,001,151 | 3/1991 | Alam et al. | 514/509 |
| 5,059,603 | 10/1991 | Rubin | 514/264 |
| 5,204,339 | 4/1993 | Minaskanian et al. | 514/182 |
| 5,242,391 | 9/1993 | Place et al. | 604/60 |
| 5,256,652 | 10/1993 | El-Rashidy | 514/58 |

OTHER PUBLICATIONS

Joy et al., Comparative Pharmacodynamics and Hemodynamics of the Topical Application to the Penis of Nitroglycerin Ointment versus An Aqueous Nitroglycerin Gel in Healthy Male Volunteers, American Urological Association, Inc., 1994 Annual Meeting, San Francisco, CA, 1994.

*Primary Examiner*—William R. A. Jarvis
*Attorney, Agent, or Firm*—Pollock, Vande Sande & Priddy

[57] ABSTRACT

A stable, uniform, water-based topical cream containing nitroglycerin, a penetration enhancer, water, a thickener and an emulsifier is provided. Also provided are the method of preparing the cream and the use of the cream for treating male erectile dysfunction or female anorgasmia. The present invention also relates to treating patients suffering from microvascular diseases or from injured tissue.

24 Claims, No Drawings

WATER-BASED TOPICAL CREAM CONTAINING NITROGLYCERIN AND METHOD OF PREPARATION AND USE THEREOF

CROSS REFERENCE TO RELATED APPLICATIONS

This is a continuation-in-part of U.S. patent application Ser. No. 08/069,409, filed Jun. 1, 1993, now abandoned, and of U.S. patent application Ser. No. 08/398,872, filed Mar. 6, 1995, now abandoned, the disclosures of which are incorporated herein by reference.

DESCRIPTION

1. Technical Field

The present invention is concerned with stable, uniform, water-based topical creams of nitroglycerin. The topical creams of the present invention are especially useful for treating erectile dysfunction and female anorgasmia. Topical creams of the present invention are also useful in stimulating blood flow to peripheral nerves in patients suffering from diabetic neuropathy and/or other microvascular diseases. Creams of the present invention also find use in stimulating hemodynamic blood flow into injured tissue.

The present invention relates to topical creams that facilitate the transdermal delivery of nitroglycerin through the dermal and epidermal layers of the penis and clitoris for treating male erectile dysfunction and female anorgasmia, respectively.

The creams of the present invention provide fast penetration of vasoactive agents into the penis and clitoris with less discomfort and transference among sexual partners.

The present invention also relates to the use of the creams for treating male erectile dysfunction and female anorgasmia. Moreover, the present invention relates to a method for preparing the topical creams of the present invention.

2. Background of the Invention

The term sexual impotence, or inhibited sexual excitement, refers to the inability of a man to achieve a quality of erection sufficient to enable him to successfully experience coitus. The cause of this impotence may be either primary or secondary. In primary impotence, the man has never been able to achieve a satisfactory erection for coitus. In secondary impotence, the man has previously been potent and usually has been able to reach coitus but has subsequently developed his impotence.

The Kinsey study (Kinsey, A. C., Pomeroy, W. B., and Martin, C. E., *Sexual Behavior in the Human Male*, W. B. Saunders, Philadelphia, 1948.) declared impotence to be a relatively rare occurrence in men up to age 35. However, with the advent of the so-called "sexual revolution" more men under this age group appear to be seeking treatment for this condition. The Kinsey statistics do reveal a gradual rise in the incidence of erectile dysfunction with age, particularly after 45, with a more rapid increase after 55. By age 75, nearly 55 percent of males reported problems, and by 80, 75 percent, However, research has shown (*The Sexual Experience*, (Sadock, Kaplan, and Freeman, eds.), Williams and Wilkins, Baltimore, 1976, Chapt. 15.4.) that aging is not an inevitable cause of impotence, even into the seventh and eighth decades of life.

Erectile dysfunction is almost always due to physical factors. Physical factors include systemic diseases (e.g. diabetes mellitus [the most common], syphilis, alcoholism, drug dependency, hypopituitarism, and hypothyroidism); local disorders (e.g. congenital abnormalities and inflammatory diseases of the genitalia); vascular disturbances such as aortic aneurysm and atherosclerosis (e.g. Leriche's syndrome): neurogenic disorders (e.g. multiple sclerosis, spinal cord lesions, pituitary microadenoma with hyperprolactinemia, and cardiovascular accident); drugs such as antihypertensives, sedatives, tranquilizers, and amphetamines; and surgical procedures such as sympathectomy. Prostatectomy and castration produce varying effects. Impotence is usually not induced by transurethral prostatectomy, whereas it almost always occurs after perineal prostatectomy. *The Merck Manual*, 16th edition, (Berkow, R., ed.), Merck Research Laboratories, Rahway, N.J., 1992, Chapt. 139.

Psychological factors, which include an abnormal fear of the vagina, sexual guilt, fear of intimacy, or depression, are the cause in about 20% of the cases of erectile dysfunction.

To date the pharmacological management of erectile dysfunction has been based mainly on the intracavernous injection of various smooth muscle relaxant drugs. Self-injection of smooth muscle relaxant drugs such as papaverine and/or prostaglandin $E_1$ alone or in combination with phentolamine has been used successfully for a number of year in the treatment of impotence. However, numerous side effects have been reported and many patients have stopped using the self-injection procedure for various reasons mainly because of the lack of spontaneity and because of the unpleasant and sometimes pathological side effects caused by this technique. Consequently, a non-invasive therapeutic alternative seems attractive.

To this end, a number of investigators have begun to utilize preparations consisting of nitroglycerin in either ointment or patch form. In a study by Meyhoff, et al. (Meyhoff, H., Rosenkilde, P., and Bodker, Al., *Brit. J. Urol.*, Vol. 68, pp. 89–90, (1992)) a nitroglycerin ointment was evaluated with good results and in a previous study by Claes and Baert (Owen, J. A., et al., *J. Urol.*, Vol. 141, pp. 546548, (1989)) a nitroglycerin ointment was used with positive results. Both types of preparations suffer from one or more of the following disadvantages. The time necessary to achieve an erection varied widely with latent periods ranging from 1 to 2 hours. Consequently, any notion of spontaneity is invalidated. Both preparations primarily use lipophilic agents, such as petroleum jelly and/or lanolin as the matrix for the nitroglycerin. These agents lead to not only a very slow release of nitroglycerin into the penile tissue but also leave an oily residue on the penile shaft such that the nitroglycerin contained in this residue is easily transferred to the partner via the vaginal mucosa. A further drawback to the use of these preparations is the production of an intense burning sensation when the material is applied to the penis.

Concerning a different problem, no medications and/or viable treatment methods are currently available for the female who suffers from inhibited sexual excitement (i.e., anorgasmia or sexual arousal disorder), even though there are certain physiological and anatomical similarities between male and female external genitalia.

In the normal man or woman, a sequence of physiological sexual responses exists that has been described by Sadock et al., in Sadock, Kaplan, and Freeman, Eds., *The Sexual Experience*, Williams and Wilkins, Baltimore, (1976), Chapter 3. These levels of sexual arousal consist of four discrete phases, each accompanied by unique physiological changes. These phases can be understood physiologically as increasing levels of vasocongestion and myotonia (tumescence) and the subsequent rapid release of this vascular activity and muscle tone as a result of orgasm (detumescence).

If the clitoris does not become engorged with blood, for any number of reasons, orgasm is not attainable. Women who present this complaint are diagnosed as having a sexual arousal disorder. This condition is more precisely defined as the persistent or recurrent failure to attain or maintain the lubrication-swelling response of sexual excitement until completion of sexual activity. This inhibition occurs despite adequate sexual stimulation in focus, intensity, and duration. The disorder may be primary or, more frequently, secondary and restricted to the partner. Psychologically acquired factors cause most of the cases of secondary dysfunction; e.g., marital discord (about 80% of the cases), depression, and stressful life situations. Ignorance of genital anatomy and function is common, particularly of clitoral function and of effective arousal patterns and techniques. Association of sex with sinfulness, and sexual pleasure with guilt, may be lifelong. Fear of intimacy may also play a part.

The physical causes include localized disease (e.g., endometriosis, cystitis, vaginitis); systemic diseases (e.g., hypothyroidism, diabetes mellitus—though its impact is greater on men); peripheral of CNS disorders (e.g., multiple sclerosis); muscular disorders (e.g., muscular dystrophy); drugs (e.g. oral contraceptives, antihypertensives, tranquilizers have variable effects); and ablative surgery (e.g., hysterectomy, mastectomy, which may have a negative impact on the woman's sexual self-image).

Besides those women in the general population, recent publications have emphasized these problems in older female populations (Osburn, M., *Brit Med. J.*, Vol. 296, pp. 959–962, (1988)), in post-menopausal women, and in those who have undergone a hysterectomy (The American College of Obstetricians, *Gynecologists Office Practice and Practice Management: Sexuality and Sexual Dysfunction*, American College of Obstetricians and Gynecologists, Chapter 10 (1986)). In addition, those women afflicted with Type II diabetes appear to suffer from an increased frequency of sexual problems, including anorgasmia (Schreiner, et al., "Diagnosing and Treating the Sexual Problems of Diabetic Women," in *Clinical Diabetes*, Vol 6, pp. 121–136 (1988)).

Although there are many reasons given for the inability of a woman to reach orgasm, one aspect of the present invention is directed toward the first phase of the sexual response cycle, the excitement phase. Since the female clitoris and its associated structures are both anatomically and embryologically similar to the male penis, it is medically correct to assume that the clitoris should (and does) respond in kind during the excitement phase of the response cycle.

Both the clitoris and the penis have corpora cavernosa, an anatomical shaft, and both are erectile. Consequently, since a satisfactory erection can be produced in impotent males by the introduction of vasoactive agents into the male members, either by injection or by transdermal methods, it follows that the same procedure(s) will be equally valid in treating women who complain of inhibited sexual excitement. However, the introduction of vasodilators or other vasoactive agents by hypodermic injection would be both impractical and dangerous.

Further, since the clitoris is much smaller than its male counterpart, has a much thinner striatum cornuium, and is more sensitive to tactile stimulation, any topical transdermal preparations containing a vasodilator must address these characteristics.

SUMMARY OF INVENTION

The present invention provides a stable, uniform, water-based cream containing nitroglycerin. The present invention overcomes the problem of the nitroglycerin precipitating out of water-based compositions.

The compositions of the present invention are especially useful for treating individuals suffering from erectile dysfunction or female anorgasmia. The compositions exhibit an improved safety profile resulting in significantly less burning, headache and transference to a partner. Moreover, the compositions of the present invention result in reduced mess and residual material after application, thereby improving "feel." Furthermore, the compositions are faster acting when compared to previously disclosed topical preparations.

Compositions of the present invention are also useful in stimulating blood flow to peripheral nerves in patients suffering from microvascular diseases, such as diabetic neuropathy. Moreover, compositions of the present invention are useful in stimulating hemodynamic blood flow into injured tissue, such as a wound or surgical incision.

The results and properties achieved by the present invention are due to the judicious selection of the ingredients and their relative amounts. More particularly, the topical cream of the present invention contains:

A) about 0.1 to about 3% by weight of nitroglycerin;

B) about 5 to about 24% by weight of a penetration enhancer;

C) about 60 to about 90% by weight of water;

D) about 0.5 to about 3% by weight of a thickener; and

E) about 0.4 to about 2% by weight of an emulsifier

In addition, the present invention is concerned with a method for treating an individual suffering from erectile dysfunction or female anorgasmia. The method comprises topically applying to the genital area of the individual, an effective amount of the above disclosed topical cream.

Another aspect of the present invention relates to treating patients suffering from a microvascular disease by topically applying to the afflicted areas of the patient an effective amount of the above disclosed topical cream. A further aspect of the present invention relates to treating patients suffering from a wound or having a surgical incision by topically applying to the area near or within the vicinity of the wound or surgical incision of the patient an effective amount of the above disclosed topical cream.

A still further aspect of the present invention relates to preparing the above disclosed topical cream. The method involves admixing the thickener and about 80 to about 90% of the water and heating to provide a first solution. Admixing the emulsifier, about 15 to about 85% of the penetration enhancer, the remaining portion of the water with heating results in a second solution. Next, admixing the first solution and second solution provides a cream base. Admixing the nitroglycerin, remaining portion of the penetration enhancer and the cream base results in the desired topical cream.

BEST AND VARIOUS MODES FOR CARRYING OUT THE PRESENT INVENTION

The stable, uniform, water-based topical cream of the present invention contains nitroglycerin as a vasodilator. The nitroglycerin is present in the cream in an amount of about 0.1 to about 3% and preferably about 0.1 to about 1% by weight.

In addition, the cream contains a penetration enhancer in an amount of about 5 to about 24%, and preferably about 8 to 13% by weight.

The preferred penetration enhancers employed, according to the present invention, are propylene glycol, glycerine, isopropyl palmitate, isopropyl myriatate, and laurocapram.

The topical creams of the present invention must contain water in an amount of about 60 to about 90%, and preferably about 75 to about 88% by weight.

The creams of the present invention also contains a thickener in an amount of about 0.5 to about 3%, and preferably about 1.1 to about 2% by weight. Preferred thickeners employed in the present invention are methylcellulose, polyethylene glycol, and acrylic acid polymers. Carbopol 934P and Carbopol 940, commercially available from B.F. Goodrich Co., when neutralized, are suitable acrylic acid polymers. A preferred polyethylene glycol is polyethylene glycol 8000. A preferred methylcellulose is methylcellulose 4000.

The creams also contain an emulsifier in an amount of about 0.4 to about 2%, and preferably about 0.4 to about 1% by weight. The emulsifier is preferably a non-ionic surface active agent. Typical non-ionic surfactants include the polysorbates, which are mixtures of partial esters of sorbitol and its mono- and dianhydrides, typically condensed with approximately 20 mol of ethylene oxide; polyethyoxylated alkyl ethers and esters, in which the alkyl chain can be either saturated, unsaturated, branched or linear; polyethoxylated alkyl phenols, in which the hydrophobic group normally octyl or nonylphenol; and poloxamers, polyoxyethylene-polyoxypropylene block copolmyers, in which the polyoxypropylene chain acts as the hydrophobic moiety.

Some commercially available non-ionic surfactants are Brij 99, Brij 78, polyoxyl 40 stearate and polysorbate 80. Brij 99 and Brij 78 are polyethylene glycol fatty alcohol ethers. Polyoxyl 40 stearate is a mixture of mono and distearate esters of polyoxyethylene and of free polyoxyethylene. Polysorbate 80 is polyoxyethylene (20) sorbitan mono-oleate.

The compositions of the present invention preferably have a pH value of about 6.5 to about 9.0. When desired, the pH value can be adjusted by adding alkyl ethanolamines and/or a suitable buffer system, such as phosphate or citrate based buffers.

The compositions of the present invention can optionally contain auxiliary ingredients, such as flavorings, fragrances, preservatives and/or coloring agents. When present, such are usually added in amounts of about 0.05 to about 0.30%. Suitable preservatives include methylparabens (methyl PABA), propylparabens (propyl PABA) and butylhydroxy toluene (BHT).

The compositions of the present invention can also include a small amount, about 0.01 to about 4% by weight, of a topical anesthetic, if desired. Typical anesthetics include lidocaine and dibucaine.

The topical creams of the present invention are preferably prepared by admixing the thickener and about 80 to about 90% of the water and heating to a temperature of about 45° C. to about 75° C. to provide a first solution. Admixing the emulsifier, about 15 to about 85% of the penetration enhancer, the remaining portion of the water with heating to a temperature of about 35° C. to about 70° C. results in a second solution. Next, admixing the first solution and second solution at a lowered temperature, preferably below about 50° C. provides a cream base. Admixing the nitroglycerin, remaining portion of the penetration enhancer and any auxiliary ingredients and the cream base, results in the desired topical cream.

To treat impotence or anorgasmia, the cream is applied to the shaft and glans of the penis or to the clitoris and massaged until absorption is complete. Amounts of the invention ranging between about 0.1 and about 10 grams and preferably about 0.1 to about 3 are sufficient for vasodilation and the erectile process to occur. The most preferred amount for treating erectile dysfunction is about 0.2 to about 3 grams, and for treating female anorgasmia is about 0.1 to about 1 gram. The present invention can be used with or without benefit of erotic stimuli. The determination of an ideal dose of the composition should be determined with each individual by one skilled in the art, such as a physician or sex therapist.

Use of the present invention in treating the problem of impotence and anorgasmia is far superior to other methods thus far proposed. It is non-invasive and offers a treatment that the sexual partner need not be aware of. It uses only ingredients that have been approved for human use by those regulatory agencies charged with such matters. It does not use penetration enhancers, such as dimethyl sulfoxide, which have not been approved for such uses. The creams of the present invention act in a relatively short time (about 5–15 minutes). In addition, in view of the long lasting ability of the compositions of the present invention, such do not require a vasoconstrictor, as required in certain prior art formulations. This invention causes vasodilation in and around the penis or clitoris, and produces an erection lasting from 15 minutes to 2 hours.

The present invention is formulated with a rapidly absorbed aqueous base so that little, if any, of the active ingredient is transferred to the sexual partner.

Compositions of the present invention, in addition to promoting the vasoactive agents to penetrate into the striatum cornium and its associated structures are also useful in stimulating blood flow to peripheral nerves in patients suffering from microvascular diseases, such as diabetic neuropathy. The abnormalities, which patients with such diseases in their platelet function exhibit including the increased blood and plasma viscosity, and the increased erythrocyte aggregability and adhesiveness lead to a reduction in capillary erythrocyte velocity. Episodes of sludging and stasis in the microcapillaries that consequently develop eventually lead to local hypoxia. Therefore, these patients will benefit from the vasodilation effect following topical application of the present invention to the skin of their afflicted area. For such uses, topical astringent, antioxidant, anti-fungal and/or moisturizing ingredients may be incorporated into select formulations. The preferred mount for treating microvascular diseases is about 1 to about 3 grams of the composition.

Furthermore, the present invention is useful in stimulating hemodynamic blood flow into injured tissue. An increase in blood flow (or the maintenance of normal flow) into such tissue ensures the presence of natural healing factors. This property of the present invention is of considerable benefit to patients who have incurred traumatic cuts, abrasions and/or surgical incisions. Fur such uses, antibiotic and/or topical anesthetics may be incorporated into selected formulations. The preferred amount used for stimulating hemodynamic blood flow into injured tissue is about 0.2 to about 1 gram of the composition.

The following non-limiting examples further illustrate compositions and dosage forms of the present invention. The compositions were prepared by the process disclosed above, unless stated otherwise.

| Example 1 | | Example 2 | |
|---|---|---|---|
| Water | 82.60% | Water | 70.75% |
| Nitroglycerin | 1.50 | Nitroglycerin | 1.00 |
| Propylene Glycol | 3.00 | Propylene Glycol | 15.00 |
| Glycerine | 5.00 | Glycerine | 5.00 |
| Isopropyl Palmitate | 1.00 | Laurocapram | 1.50 |
| Polyethylene Glycol 8000 | 0.50 | Isopropyl Palmitate | 1.00 |

| Carbopol 940 | 1.50 | Methylcellulose | 1.80 |
|---|---|---|---|
| Polyoxyl 40 Stearate | 0.50 | Carbomer 934P | 1.05 |
| Brij 78 | 1.00 | Brij 78 | 1.50 |
| Triethanolamine | 2.00 | Triethanolamine | 1.00 |
| Sodium Borate | 0.30 | Sodium Borate | 0.25 |
| Butylated Hydroxytoluene | 0.02 | Butylated Hydroxytoluene | 0.05 |
| Methyl Parabens | 0.02 | Methyl Parabens | 0.05 |
| Flavoring Agents | 0.04 | Propyl Parabens | 0.05 |

| Example 3 | | Example 4 | |
|---|---|---|---|
| Water | 83.00% | Water | 83.00% |
| Nitroglycerin | 0.50 | Nitroglycerin | 1.50 |
| Propylene Glycol | 5.00 | Propylene Glycol | 5.00 |
| Glycerine | 3.00 | Glycerine | 3.00 |
| Isopropyl Myristate | 1.00 | Laurocapram | 1.00 |
| Carbopol 934P | 1.10 | Carbomer 934P | 0.80 |
| Grape Seed Oil | 0.50 | Light Mineral Oil | 0.50 |
| Cocoa Butter | 1.00 | Methylcellulose | 1.00 |
| Brij 99 | 2.00 | Brij 99 | 1.50 |
| Triethanolamine | 2.00 | Triethanolamine | 1.50 |
| Potassium Phosphate | 0.83 | Disodium Phosphate | 1.00 |
| Methyl Parabens | 0.02 | Methyl Parabens | 0.02 |
| Propyl Parabens | 0.02 | Propyl Parabens | 0.02 |
| Flavoring | 0.02 | Fragrance | 0.02 |
| | | Flavorings | 0.14 |

| Example 5 | | Example 6 | |
|---|---|---|---|
| Water | 86.00% | Water | 84.46% |
| Nitroglycerin | 0.75 | Nitroglycerin | 1.00 |
| Propylene Glycol | 6.75 | Propylene Glycol | 9.00 |
| Isopropyl Palmitate | 2.00 | Isopropyl Palmitate | 2.00 |
| Methylcellulose, 4000 | 0.40 | Carbopol 934P | 0.70 |
| Carbopol 934P | 0.70 | Methylcellulose | 0.40 |
| Polyethylene Glycol 8000 | 0.50 | Polyethylene Glycol 8000 | 0.50 |
| Brij 99 | 1.00 | | |
| Polyoxyl 40 Stearate | 0.50 | Brij 99 | 0.50 |
| Triethanolamine | 1.00 | Triethanolamine | 1.20 |
| Sodium Borate | 0.20 | Sodium Borate | 0.20 |
| Methyl Parabens | 0.02 | Methyl Parabens | 0.02 |
| Propyl Parabens | 0.02 | Propyl Parabens | 0.02 |
| Fragrance | 0.14 | Butylated Hydroxytoluene | 0.02 |
| Coloring | 0.02 | Fragrance | 0.15 |
| | | Coloring | 0.02 |

| Example 7 | | Example 8 | |
|---|---|---|---|
| Water | 84.46% | Water | 81.47 |
| Nitroglycerin | 0.20 | Nitroglycerin | 0.75% |
| Propylene Glycol | 9.80 | Dibucaine | 2.00% |
| Isopropyl Palmitate | 2.00 | Propylene Glycol | 9.25 |
| Carbopol 934P | 0.70 | Isopropyl Myristate | 3.00 |
| Methylcellulose, 4000 | 0.40 | Carbopol 930P | 0.50 |
| Polyethylene Glycol 8000 | 0.50 | Methylcellulose, 4000 | 0.40 |
| Brij 99 | 0.50 | Polyethylene Glycol 8000 | 0.50 |
| Triethanolamine | 1.20 | Brij 99 | 0.50 |
| Sodium Borate | 0.20 | Triethanolamine | 1.20 |
| Methyl Parabens | 0.02 | Sodium Borate | 0.20 |
| Propyl Parabens | 0.02 | Methyl Parabens | 0.02 |
| Butylated Hydroxytoluene | 0.02 | Propyl Parabens | 0.02 |
| Fragrance | 0.15 | Butylated Hydroxytoluene | 0.02 |
| Coloring | 0.03 | Fragrance | 0.15 |
| | | Coloring | 0.02 |

| Example 9 | |
|---|---|
| Water | 80.27 |
| Nitroglycerin | 1.00% |
| Lidocaine | 4.00% |
| Propylene Glycol | 9.00 |
| Isopropyl Palmitate | 2.00 |
| Carbopol 934P | 0.70 |
| Methylellulose, 4000 | 0.40 |
| Polyethylene Glycol 8000 | 0.50 |
| Brij 99 | 0.50 |
| Triethanolamine | 1.20 |
| Sodium Borate | 0.20 |
| Methyl Parabens | 0.02 |
| Propyl Parabens | 0.02 |
| Butylated Hydroxytoluene | 0.02 |
| Fragrance | 0.15 |
| Coloring | 0.02 |

What is claimed is:

1. A stable, uniform, water-based topical cream comprising:

a) about 0.1 to about 3% by weight of nitroglycerin;

b) about 5 to about 24% by weight of a penetration enhancer;

c) about 60% to about 90% by weight of water;

d) about 0.5 to about 3% by weight of a thickener; and e) about 0.4 to about 2% by weight of an emulsifier.

2. The cream of claim 1 wherein the amount of said nitroglycerin is about 0.1 to about 1% by weight.

3. The cream of claim 1 wherein the amount of said penetration enhancer is about 8 to about 13% by weight.

4. The cream of claim 1 wherein said penetration enhancer is at least one member selected from the group consisting of propylene glycol, glycerine, isopropyl palmitate, isopropyl myristate, laurocapram, and mixtures thereof.

5. The cream of claim 1 wherein the amount of water is about 75 to about 88% by weight.

6. The cream of claim 1 wherein the amount of said thickener is about 1.1 to about 2% by weight.

7. The cream of claim 1 wherein said thickener is at least one member selected from the group consisting of methylcellulose, polyethylene glycol, acrylic acid polymers and mixtures thereof.

8. The cream of claim 1 wherein said emulsifier is an amount of about 0.4 to about 1% by weight.

9. The cream of claim 1 wherein said emulsifier is a non-ionic surface active agent.

10. The cream of claim 1 wherein said emulsifier is at least one member selected from the group consisting of polyethylene glycol alcohol ether, polyoxyethylene acid ester, and partial ester of sorbitol or anhydride thereof; and mixtures thereof.

11. The cream of claim 1 having a pH of about 6.0 to about 8.0.

12. The cream of claim 11 containing an alkyl ethanolamine or buffer or both.

13. The cream of claim 11 that contains at least one member selected from the group of flavorings, fragrances, preservatives, coloring agents, topical anesthetics, and mixtures thereof.

14. A method for treating a male patient suffering from erectile dysfunction which comprises topically applying to the genital area of said patient an effective mount of the topical cream of claim 1.

15. The method of claim 14 for treating a patient suffering from erectile dysfunction by applying about 0.2 to about 3 grams of said cream.

16. A method for treating a female patient suffering from anorgasmia which comprises topically applying to the vaginal area of said patient an effective amount of the topical cream of claim 1.

17. The method of claim 16 for treating a patient suffering from anorgasmia by applying about 0.1 to about 1.10 grams of said cream.

18. A method for treating a patient suffering from a microvascular disease which comprises topically applying to the afflicted areas of said patient an effective amount of the topical cream of claim 1.

19. The method of claim 18 wherein said microvascular disease is peripheral neuropathy.

20. The method of claim 18 which comprises applying about 1 to about 3 grams of said cream.

21. A method for treating a patient suffering from a wound or surgical incision which comprises topically applying to the area within the vicinity of said wound or incision of said patient an effective amount of the topical cream of claim 1.

22. The method of claim 21 which comprises applying about 0.2 to 1 gram of said cream.

23. A method for preparing the topical cream of claim 1 which comprises:

admixing said thickener and about 80 to about 90% of the water and heating to provide a first solution;

admixing said emulsifier, about 15 to about 85% of said penetration enhancer, the remainder of said water with heating to provide a second solution;

admixing said first solution and said second solution to provide a cream base; and admixing said nitroglycerin, the remainder of said penetration enhancer and the cream base to obtain said topical cream.

24. The method of claim 23 wherein said first solution and said second solution are admixed at a temperature of about 50° C. or lower.

* * * * *